(12) United States Patent
Wang et al.

(10) Patent No.: US 10,772,579 B2
(45) Date of Patent: Sep. 15, 2020

(54) SYSTEMS AND METHODS FOR REDUCING RADIATION DOSE IN CT

(71) Applicant: THE REGENTS OF THE UNIVERSITY OF CALIFORNIA, Oakland, CA (US)

(72) Inventors: Danny J J Wang, Oak Park, CA (US); Thomas Martin, Los Angeles, CA (US); John M. Hoffman, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 196 days.

(21) Appl. No.: 15/824,862

(22) Filed: Nov. 28, 2017

(65) Prior Publication Data
US 2018/0132800 A1 May 17, 2018

Related U.S. Application Data

(63) Continuation of application No. PCT/US2016/035116, filed on May 31, 2016.
(Continued)

(51) Int. Cl.
*A61B 6/00* (2006.01)
*A61B 6/03* (2006.01)
(Continued)

(52) U.S. Cl.
CPC ............... *A61B 6/035* (2013.01); *A61B 6/02* (2013.01); *A61B 6/032* (2013.01); *A61B 6/06* (2013.01);
(Continued)

(58) Field of Classification Search
CPC .......... A61B 6/02; A61B 6/032; A61B 6/035; A61B 6/06; A61B 6/40; A61B 6/405;
(Continued)

(56) References Cited

U.S. PATENT DOCUMENTS 4,200,800 A * 4/1980 Swift ...................... H05G 1/34
378/10
7,123,680 B2 1/2006 Katada
(Continued)

FOREIGN PATENT DOCUMENTS

WO 2014085288 A1 6/2014

OTHER PUBLICATIONS

Korean Intellectual Property Office (KIPO), International Search Report and Written Opinion dated Sep. 12, 2016, counterpart PCT international application No. PCT/US2016/035116, pp. 1-13, with claims searched, pp. 14-21.
(Continued)

*Primary Examiner* — Irakli Kiknadze
(74) *Attorney, Agent, or Firm* — O'Banion & Ritchey LLP; John P. O'Banion (57) ABSTRACT

A low-dose CT imaging system and method that operates according to a pulsed X-ray emission scheme according to a predefined sequence of rotation angles of the X-ray source, along with image reconstruction algorithms to achieve high spatial and temporal resolution for CT scans. The systems and methods involve high speed switching (on the order of milliseconds) to generate pulsed exposure of X-ray radiation to the patient, reducing radiation dose by 4-8 fold, or more.

16 Claims, 6 Drawing Sheets

Related U.S. Application Data (60) Provisional application No. 62/169,498, filed on Jun. 1, 2015.

(51) Int. Cl.

| | | |
|---|---|---|
| *A61B 6/06* | (2006.01) | |
| *G06T 11/00* | (2006.01) | |
| *H05G 1/56* | (2006.01) | |
| *A61B 6/02* | (2006.01) | |
| *H01J 35/30* | (2006.01) | |
| *H05G 1/60* | (2006.01) | |
| *G21K 1/02* | (2006.01) | |

(52) U.S. Cl.
CPC ............... *A61B 6/40* (2013.01); *A61B 6/405* (2013.01); *A61B 6/542* (2013.01); *G06T 11/005* (2013.01); *G06T 11/006* (2013.01); *G21K 1/02* (2013.01); *H01J 35/30* (2013.01); *H05G 1/56* (2013.01); *H05G 1/60* (2013.01); *G06T 2211/412* (2013.01); *G06T 2211/421* (2013.01); *Y10S 378/901* (2013.01)

(58) Field of Classification Search
CPC ....... A61B 6/542; A61B 6/027; A61B 6/4441; A61B 6/488; A61B 6/481; A61B 6/482; A61B 6/504; A61B 6/544; A61B 5/0456; A61B 6/03; A61B 6/433; A61B 5/055; A61B 5/7267; A61B 6/107; A61B 6/4035; A61B 6/487; A61B 6/4028; A61B 6/4241; A61B 6/461; A61B 6/463; A61B 6/541; A61B 6/469; A61B 6/5258; A61B 6/54; A61B 2090/0436; A61B 2090/0481; A61B 2562/164; A61B 5/0088; A61B 5/682; G06T 11/005; G06T 11/006; G06T 2211/412; G06T 2211/421; G06T 7/0012; G06T 2207/10096; G06T 2207/30081; G06T 2207/30096; G21K 1/02; H01J 35/30; H05G 1/56; H05G 1/60; G01N 21/3581; G01N 33/57434
USPC .......................................... 378/4, 15, 16, 19
See application file for complete search history.

(56) References Cited

U.S. PATENT DOCUMENTS

| | | | | |
|---|---|---|---|---|
| 7,476,027 | B2 * | 1/2009 | Takenaka | G01N 23/04 378/116 |
| 9,031,190 | B2 * | 5/2015 | Tsujii | A61B 6/4452 378/108 |
| 9,795,344 | B2 * | 10/2017 | Cho | A61B 6/405 |
| 2006/0008048 | A1 | 1/2006 | Katada | |
| 2006/0115050 | A1 | 6/2006 | Resnick | |
| 2007/0092058 | A1 | 4/2007 | Mattson | |
| 2008/0056432 | A1 | 3/2008 | Pack | |
| 2008/0144765 | A1 | 6/2008 | Flohr | |
| 2010/0038973 | A1 | 2/2010 | Bleukx | |
| 2010/0046712 | A1 | 2/2010 | Behling | |
| 2010/0104062 | A1 | 4/2010 | Wu | |
| 2010/0135455 | A1 | 6/2010 | Chiang | |
| 2010/0215141 | A1 | 8/2010 | Kondo | |
| 2012/0057671 | A1 | 3/2012 | Grass | |
| 2013/0272504 | A1 | 10/2013 | Deutsch | |
| 2014/0355736 | A1 * | 12/2014 | Harada | H05G 1/46 378/16 |
| 2015/0098548 | A1 | 4/2015 | Bathe | |

OTHER PUBLICATIONS

European Patent Office (EPO), Communication (extended European search report) dated Jan. 18, 2019, related European patent application No. 16804265.3, pp. 1-11, claims searched, pp. 13-15.

* cited by examiner

SYSTEMS AND METHODS FOR REDUCING RADIATION DOSE IN CT

CROSS-REFERENCE TO RELATED APPLICATIONS

This application is a 35 U.S.C. § 111(a) continuation of PCT international application number PCT/US2016/035116 filed on May 31, 2016, incorporated herein by reference in its entirety, which claims priority to, and the benefit of, U.S. provisional patent application Ser. No. 62/169,498 filed on Jun. 1, 2015, incorporated herein by reference in its entirety. Priority is claimed to each of the foregoing applications.

The above-referenced PCT international application was published as PCT International Publication No. WO 2016/196521 on Dec. 8, 2016, which publication is incorporated herein by reference in its entirety.

STATEMENT REGARDING FEDERALLY SPONSORED RESEARCH OR DEVELOPMENT

This invention was made with Government support under EB014922, awarded by the National Institutes of Health. The Government has certain rights in the invention.

INCORPORATION-BY-REFERENCE OF COMPUTER PROGRAM APPENDIX

Appendix A referenced herein is a computer program listing in a text file entitled "UC-2014-9AC-2-LA-US-appendix-A.txt" created on Nov. 28, 2017 and having a 18 kb file size. The computer program code, which exceeds 300 lines, is submitted as a computer program listing appendix through EFS-Web and is incorporated herein by reference in its entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to medical imaging, and more particularly to X-ray computed tomography (CT) systems and methods.

2. Background Discussion

X-ray computed tomography (CT) is commonly used in clinical practice. Compared to Magnetic Resonance Imaging (MRI), CT has the advantages of fast imaging speed and fewer contraindications, however radiation is a major concern for patient safety and long term health. In particular, dynamic CT scans such as CT perfusion (CTP) and CT angiography (CTA) involve high radiation dose due to the X-ray source remaining continuously on during the scan period (e.g. one minute). Over recent years, several adverse events of CT radiation overdose have been reported by media, and radiation dose has become a public health concern. The standard CT scan involves continuous rotation of the X-ray source around the patient. According to the Nyquist criterion, a total of $\pi/2*Xres$ (base resolution) projection views need to be acquired to form one CT image. For dynamic CT scans, the total number of X-ray projection views will be $\pi/2*Xres*Nframe$ (number of temporal frames, typically 45-60 for CT), resulting in a high level of radiation dose.

Accordingly, an object of the present disclosure is CT systems and methods to reduce radiation exposure.

BRIEF SUMMARY

An aspect of the present description is low-dose CT imaging system and method that operates according to a pulsed X-ray emission scheme according to a predefined sequence of rotation angles of the X-ray source, along with image reconstruction algorithms to achieve high spatial and temporal resolution for CT scans. The systems and methods involve high speed switching (on the order of milliseconds) to generate pulsed exposure of X-ray radiation to the patient, reducing radiation dose by 4-8 folds or more compared to standard CT scans, without degrading image quality. The systems and methods of the present description allow for body CT perfusion scans that were previously not feasible due to the high radiation dose.

In one embodiment, the system of the present description may include hardware and software components, wherein the hardware allows a user to adjust dose reduction via number of projections acquired and obtain projections at predefined sequences of angles that are optimized for the reconstruction software. Novel projection view sharing techniques may be implemented, as well as iterative and/or constrained reconstruction algorithms. Three representative sequences for rotation angles may include, but are not limited to 1) angle-bisect (or bit-reverse); 2) golden-ratio; and 3) pseudo-random schemes.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 4A through FIG. 4C show various projections orders in accordance with scanning methods used in the system of the present description.

DETAILED DESCRIPTION

Figure 1:
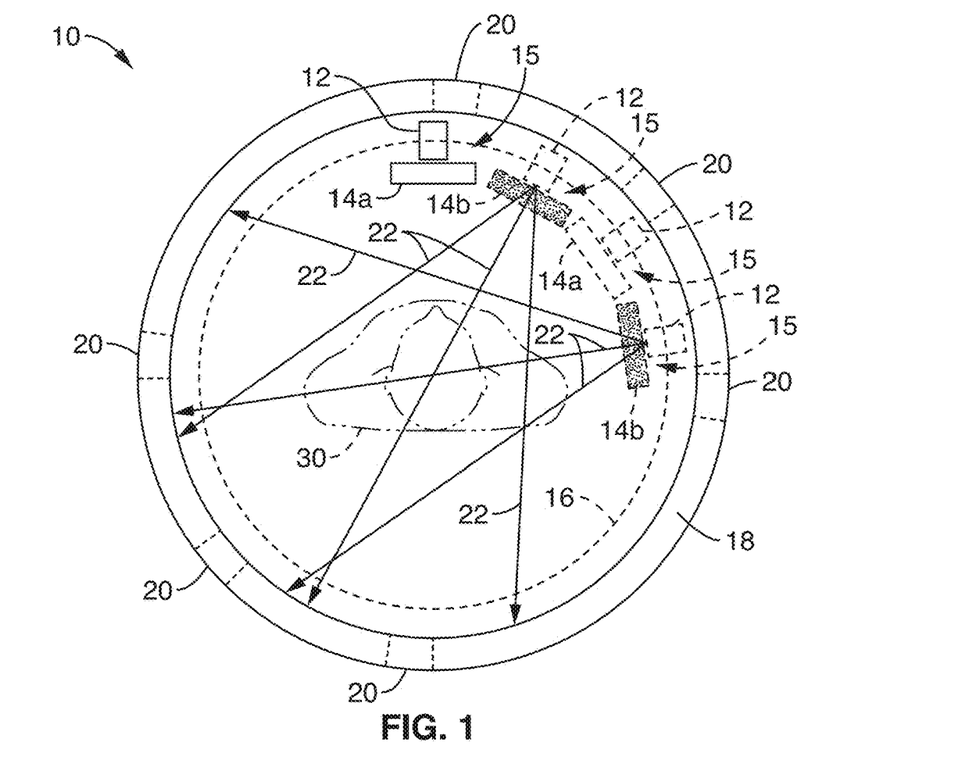
FIG. 1 shows a schematic diagram of a low-dose CT scanning system according to an embodiment of the technology of this disclosure.

FIG. 1 shows a side-view schematic diagram of a low-dose CT scanning system 10 according to the present disclosure. Low-dose CT scanning system 10 reduces the radiation dose of CT scans by controlling the X-ray source to be on intermittently (instead of continuously) at pre-specified rotation angles. The dynamic CT image series can then be reconstructed using algorithms that preserve high spatial and temporal resolutions as well as image quality comparable to those of standard scans.

The CT scanning system 10 comprises a cylindrical enclosure 18 with a plurality of detectors 20 disposed circumferentially in a stationary ring along the inner wall of the X-ray enclosure 18. While a handful of detectors 20 are shown in the side view of FIG. 1, it is appreciated that any number of detectors 20 may be used incrementally along the circumference of the ring. Additionally, a number of rings or rows may be disposed axially down the tube 18.

An X-ray source 12 is disposed in the enclosure 18 on a gantry 16 that rotates around the circumference of the inner wall of tube 18. FIG. 1 shows the X-ray source 12 in four orientations (e.g. starting from 12 o'clock to 3 o'clock) in FIG. 1. An X-ray pulse generator 15 is integrated with or attached to the X-ray source 12 to control the emission of X-rays from the source into the enclosure 18. Pulse generator 15 is shown in FIG. 1 as being disposed in front of X-ray source 12. However, it is appreciated that the pulse generator 15 may be implemented within X-ray source 12, as will be explained in further detail below.

As seen in FIG. 1, a simplistic emission scenario is depicted wherein the pulse generator 15 is alternating between an off-state at 14a and an on-state at 14b. In the off-state 14a, no X-rays are emitted from the source 12. In the on state—14b, the pulse generator 15 allows X-rays 22 to be emitted into the enclosure 18, passing through the patient 30 for detection by one or more detectors 20 on the opposite wall of the enclosure 18.

The pulse generator 15 may comprise different configurations having distinct principles of operation. In one embodiment, the pulse generator 15 comprises a mechanical shutter or lead shield that acts as blinds or a shutter that opens and closes at high speed (on the order of milliseconds) while the source 12 is continuously powered. The shutter is configured to restrict emission of X-rays 22 in the off-state 14a, and opens up to allow emission X-rays 22 in the on-state 14b.

In an alternative embodiment, the pulse generator 15 operates via electromagnetic means using the modified X-ray source 80 shown in FIG. 5A and FIG. 5B, described in further detail below.

Figure 2:
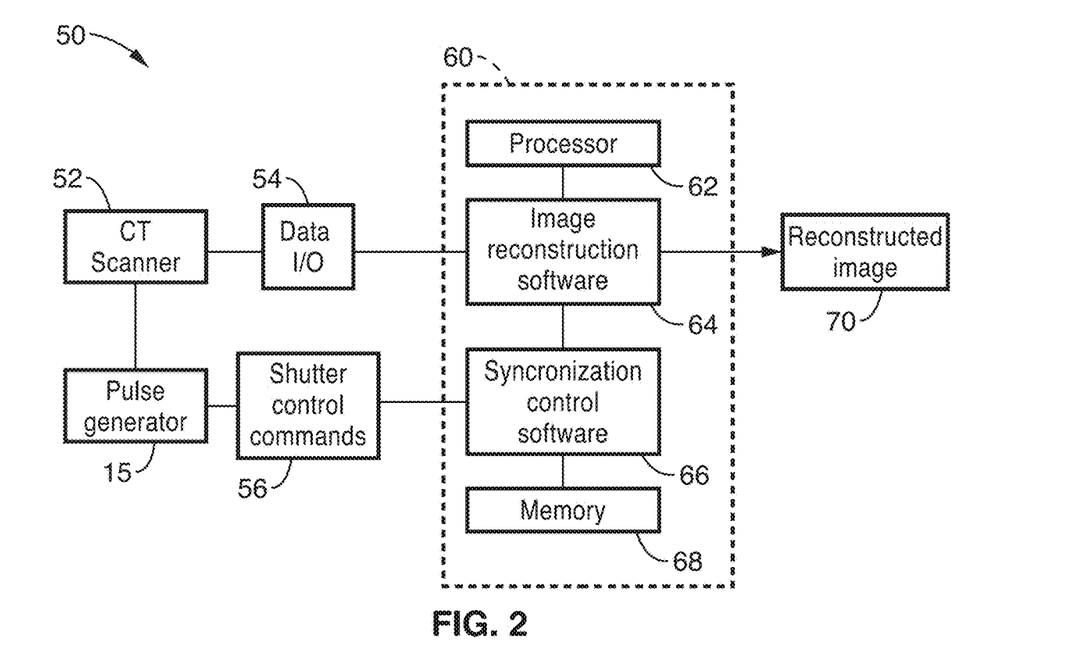
FIG. 2 shows a high-level block diagram of hardware and software components used for the low-dose CT scanning system.

FIG. 2 shows a high-level block diagram of hardware and software components used for the low-dose CT scanning system 50. From the hardware perspective, an existing CT scanner 52 is equipped with a pulse generator 15 for modulating the X-ray emission from the X-ray source 12 within in the scanner. It is appreciated that scanner 52 may be integrated with the pulse generator 15, either with a mechanical shutter built in to the source 12, or via electromagnetically pulsed operation via a modified CT X-ray source 12a/12b shown in FIG. 5A and FIG. 5B.

On the software end, computer or server 60 may comprise image reconstruction software 64, synchronization control software 66 stored in memory 68 and operable on processor 62. Synchronization control software 66 contains instructions for operating pulse generator 15, in the form of shutter control commands 56 that control the timing of the pulsing of the X-rays, as will be described in further detail below. Image reconstruction software 64 comprises instructions for taking the output data 54 from the CT scanner 52 and reconstructing the data detected from the pulsed X-ray emission to generate a reconstructed image 70.

Synchronization control software 66 is configured to control sequencing of the pulsing as the gantry 16 rotates the X-ray source 12 within the enclosure 18.

Figure 3:
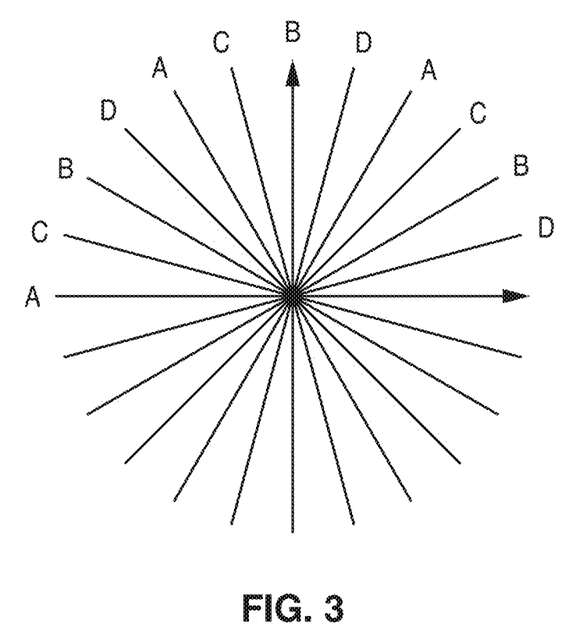
FIG. 3 shows an angle-bisect or bit-reverse scheme with 4 rotations (A, B, C, D) according to a CT exposure scheme of the present description.

In one embodiment illustrated in FIG. 3, synchronization control software 66 uses angle-bisect or bit-reverse sequence for the rotation angle at which X-ray exposure occurs. In the angle-bisect or bit-reverse scheme the full projection angles are acquired in an interleaved fashion (A, B, C, D). During the first gantry rotation, only one set of evenly distributed projection angles are acquired at position A (e.g. at 60° intervals). During subsequent gantry 16 rotations, projections that bisect the previous set of projections are acquired (position B intersects previous A positions, position C intersects A to B positions, and position D then intersects B to A positions) until the full projection angles are reached.

Figure 4A:
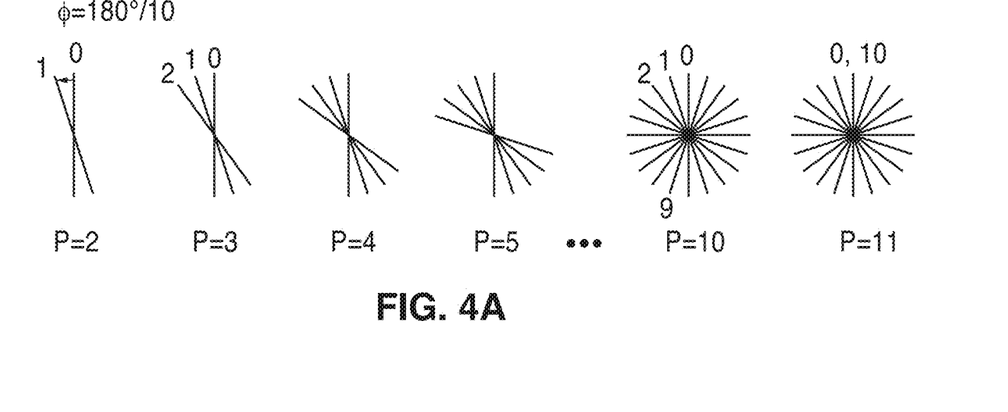
FIG. 4A, standard projection order based on a fixed increment (P=10)
Figure 4B:
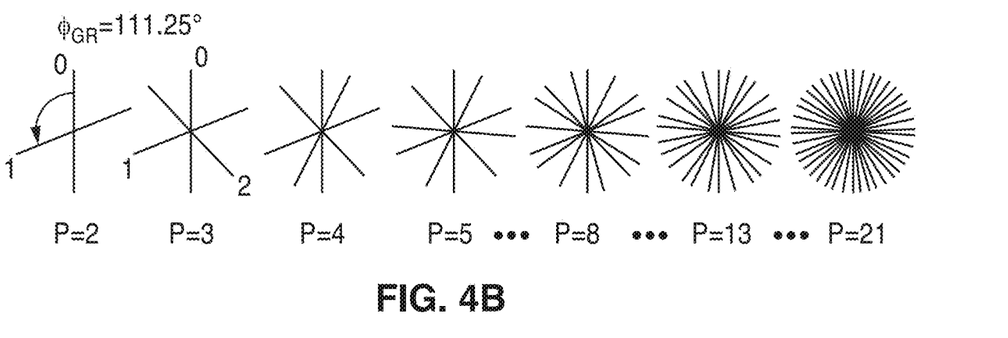
FIG. 4B, projection order based on the Golden angle increment of 111.25°, and FIG. 4C, projection order based on the Tiny Golden angle increment of 23.62°.
Figure 4C:
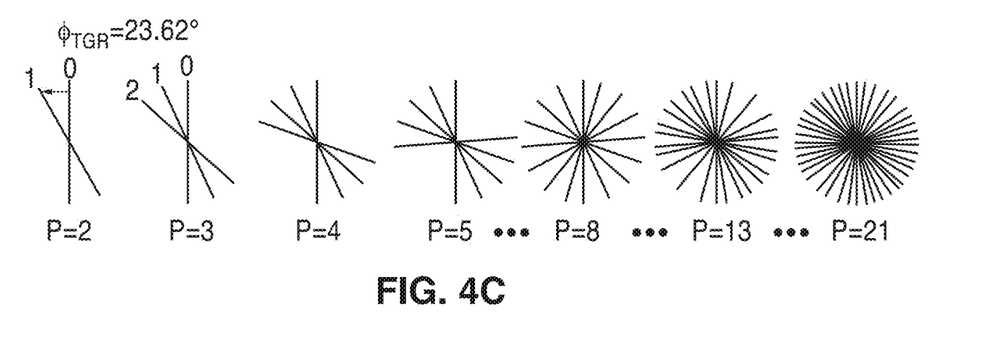

FIG. 4A through FIG. 4C show various projection orders in accordance with other scanning methods that may be implemented in the control software 66 of the system 50. FIG. 4A shows a standard projection order based on a fixed increment (P=10), or 18° projection increments.

FIG. 4B shows a projection order based on the Golden angle increment of 111.25°. In this configuration, the rotation angles of the X-ray source 12 are spaced by the golden angle (180°/1.618=111.25° which guarantees an optimal projection distribution for any arbitrary number of projections used in reconstruction.

FIG. 4C shows a projection order based on the Tiny Golden angle increment of 23.62°. In this configuration, the rotation angles of the X-ray source 12 are spaced by the angle 23.62°, which guarantees an optimal projection distribution with the number of projections is greater than 7 for the shown angle increment.

Pseudo-random schemes may also be implemented, which are optimized for modern sparse sampling techniques with constrained reconstruction, such as compressed sensing.

Figure 5A:
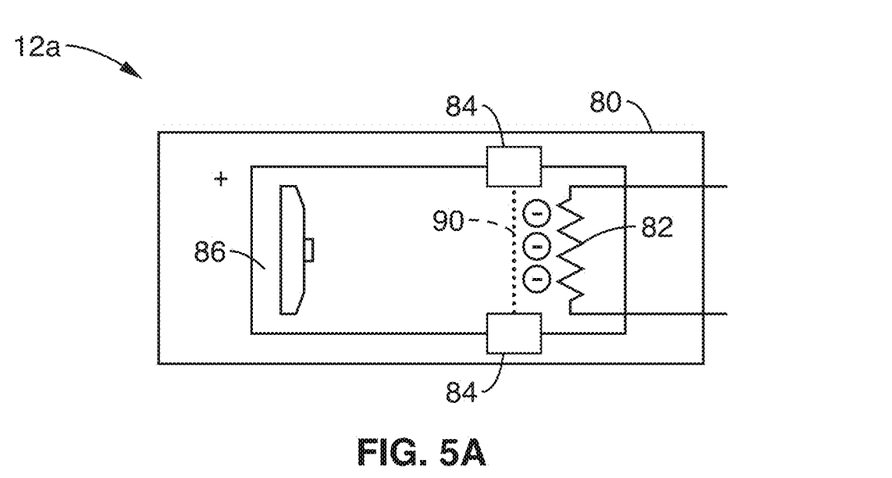
FIG. 5A shows a schematic diagram of an exemplary pulsed X-ray CT tube in a closed, non-illuminating mode in accordance with an embodiment the present description.
Figure 5B:
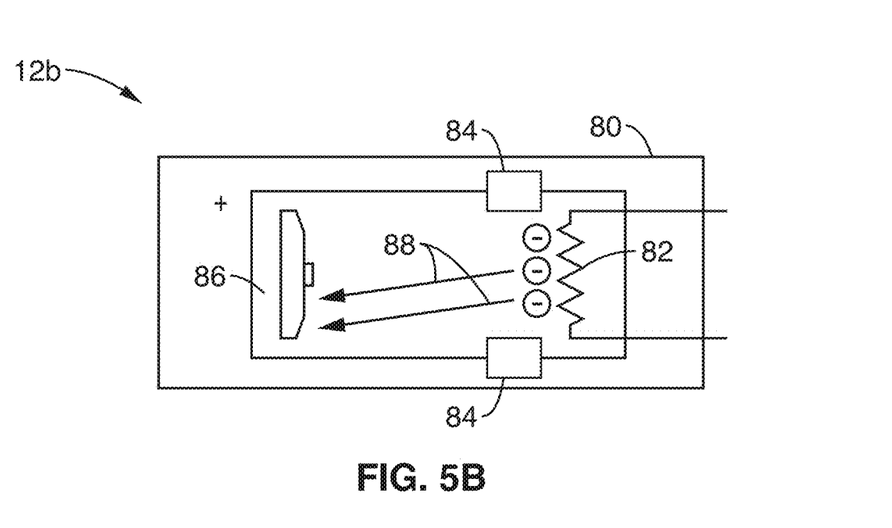
FIG. 5B shows a schematic diagram of an exemplary pulsed X-ray CT tube in an open, illuminating mode in accordance with an embodiment the present description.

Referring to FIG. 5A and FIG. 5B, high-speed power switching of the X-ray source 12 may be realized with a pulse generator 15 that operates via deflection of the electron beam off the tube anode using a magnetic field.

FIG. 5A shows a schematic diagram of an exemplary pulsed X-ray CT tube 80 in a closed, non-illuminating mode 12a. In this configuration, the griddling electrode 84 is configured to have a high enough negative potential so as to prevent electron flow from the cathode 82, essentially forming an electromagnetic field-based shield or barrier 90 between cathode 82 and anode 86. Production of X-rays is stopped, allowing for pulsed distribution of X-rays into the enclosure 18.

FIG. 5B shows a schematic diagram of the pulsed X-ray CT tube 80 in an open, illuminating mode 12b. In this mode, the griddling electrode 84 potential is modified to focus the electron beam 88 on to the anode 86, resulting in generation of the X-rays from the source 12b.

Figure 6:
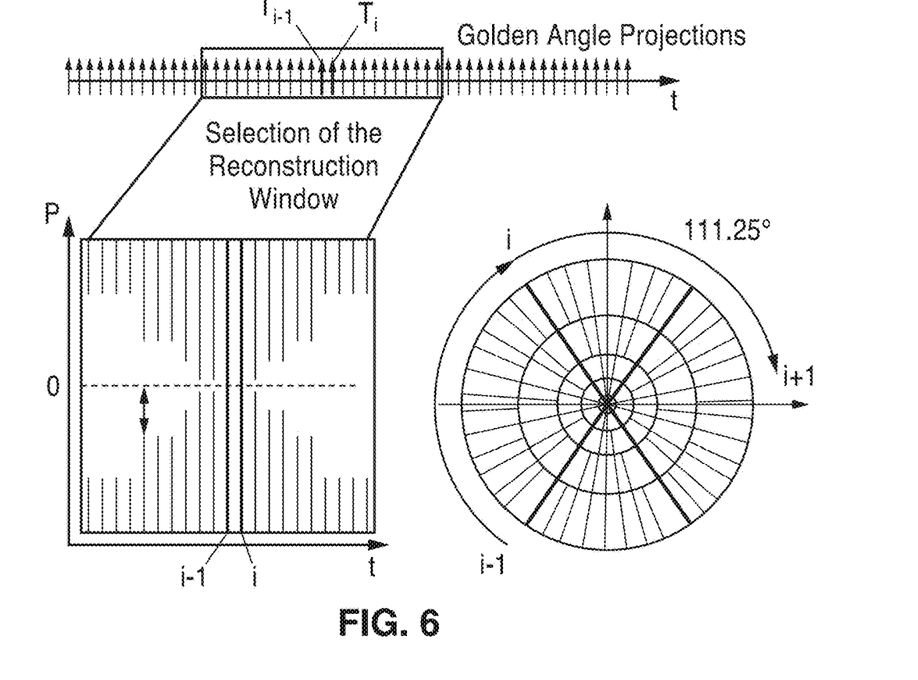
FIG. 6 shows a detailed diagram of the KWIC image reconstruction for the golden angle projection method of FIG. 4B.
Figure 7A:
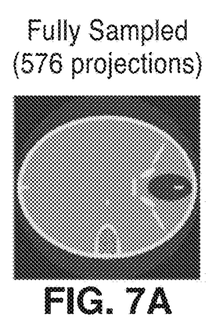
FIG. 7A through FIG. 7D show dynamic, simulated CT phantoms of a 5 mm object (white dot) using FBP with varying projections.
Figure 7B:
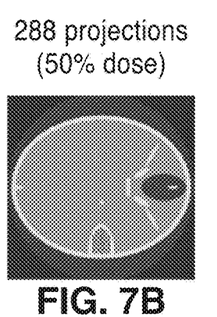
Figure 7C:
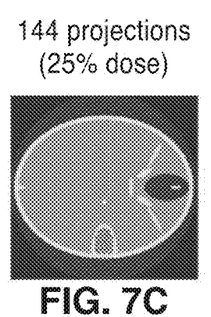
Figure 7D:
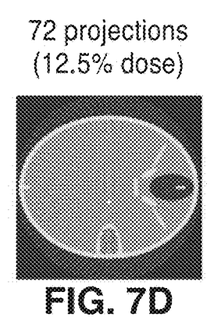
Figure 7E:
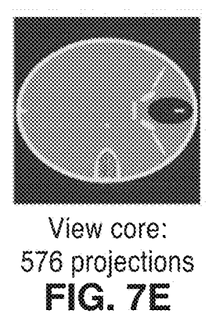
FIG. 7E through FIG. 7H show dynamic, simulated CT phantoms a 5 mm object (white dot) using KWIC with varying projections.
Figure 7F:
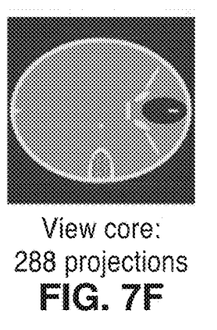
Figure 7G:
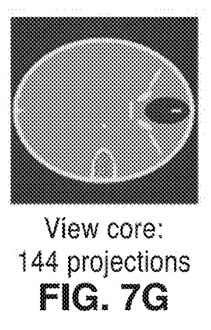
Figure 7H:
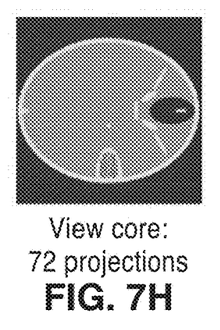

To reconstruct the full set of dynamic CT images 70, image reconstruction software 64 may incorporate projection view sharing techniques such as K-space Weighted Image Contrast (KWIC). KWIC may be implemented for any of the angle-bisect scheme (FIG. 4A) Golden angle scheme (FIG. 4B) or Tiny Golden angle scheme (FIG. 4C) for projection acquisition rotation angles of the X-ray source. FIG. 6 shows a diagram of KWIC reconstruction of dynamic CT scanning with golden angle projections. Using KWIC, the central 2DFT space (similar to k-space in MRI), which determines the image contrast, is sampled by the projection views of the time frame of interest (Ti−1, Ti in FIG. 6), whereas the peripheral 2DFT space is filled by projection views of neighboring time frames (similar to view sharing). Therefore, both high spatial and temporal resolutions can be achieved for dynamic CT scans using KWIC for any of the Golden ratio, Tiny Golden ratio, and Bit-reverse schemes, as KWIC preserves undersampled CT image quality by proportionately increasing the number of encoded projections for more distant regions of the 2D Fourier Transform (FT) space. The image reconstruction software 64 employing KWIC is able to achieve a 10 fold reduction of radial projection views compared to standard techniques, which can be translated to 10 fold reduction of radiation dose for dynamic CT scans. Alternative reconstruction techniques may also include compressed sensing.

Appendix A shows an example of software code for implementing the CT KWIC reconstruction algorithm, which provides an exemplary configuration of instructions that may be used for image reconstruction software 64.

The aforementioned KWIC reconstruction techniques were applied on a FORBILD CT head phantom as well as a clinical CT perfusion data set, resulting in a simulated 4-8× dose reduction while preserving the image quality and quantification accuracy for perfusion parameters.

FIG. 7A through FIG. 7D show dynamic, simulated CT phantoms of a 5 mm object (white dot) using standard filtered back projection (FBP) construction with full radiation dose with varying amounts of projections. FIG. 7E through FIG. 7H show dynamic, simulated CT phantoms of the same 5 mm object (white dot) using the CT-KWIC reconstruction with the same varying amounts of projections. The total number of projections per gantry rotation was reduced to obtain down to 12.5% of the original dose. The KWIC reconstruction algorithm preserves image quality that is lost to sampling artifacts in FBP.

Figure 8:
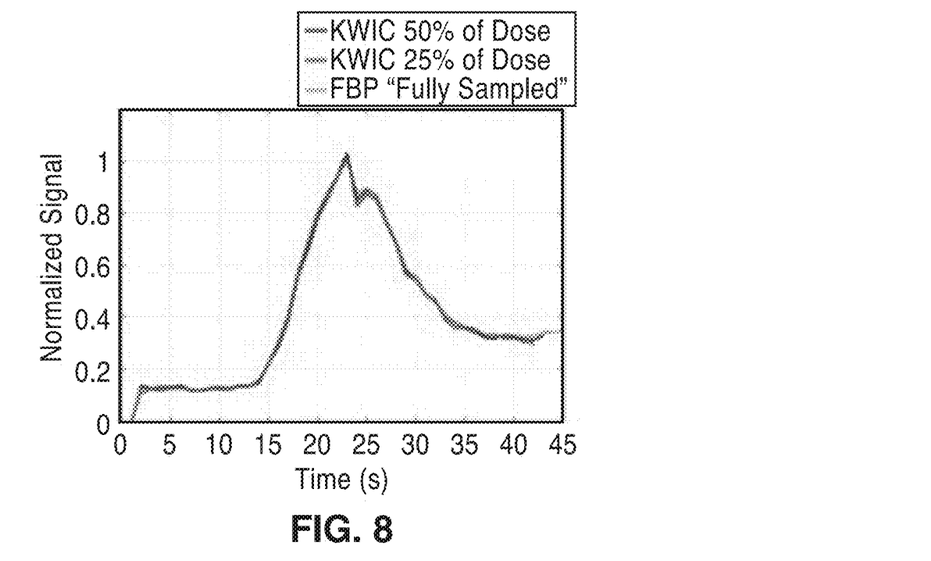
FIG. 8 shows a graph of clinical CT perfusion (CTP) signal curves of contrast uptake

It is contemplated that even higher dose savings may be possible with refinements to the CT-KWIC reconstruction algorithm used for this demonstration. FIG. 8 shows a graph of clinical CT perfusion (CTP) signal curves of contrast uptake for KWIC at 50% dose, 25% dose, and fully sampled FBP.

Figure 9A:
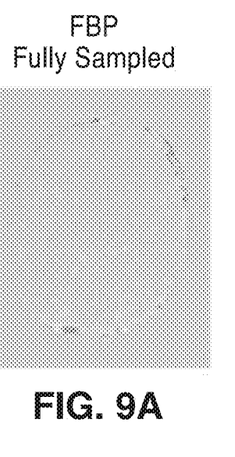
FIG. 9A and FIG. 9B show relative CBV (rCBV) maps reconstructed using FBP and KWIC, respectively. The temporal fidelity is preserved with up to 25% dose reduction using KWIC.
Figure 9B:
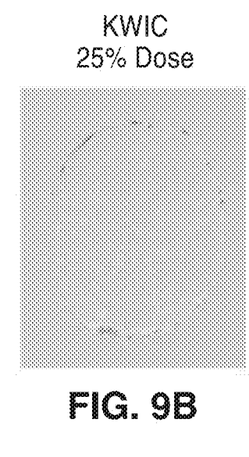

FIG. 9A and FIG. 9B show relative CBV (rCBV) maps reconstructed using FBP and KWIC, respectively. The temporal fidelity is preserved with up to 25% dose reduction using KWIC.

The systems and methods of the present description are shown in a preferred configuration directed to dynamic CT. However, it is appreciated that systems and methods of the present description may be configured for implementation with other CT imaging modalities.

The low-dose dynamic CT systems and methods described herein provide for precise CT imaging with substantially reduced dose to patients undergoing CT perfusion and angiographic exams. The low-dose dynamic CT systems and methods may be configured to allow patients to have multiple low dose CTP and CTA exams for more frequent and regular monitoring of their diseases, which could improve patient outcome. Such dose reductions may also allow for body perfusion (e.g. in the liver or kidneys) where it has previously been too high dose to be a viable diagnostic or study option.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A system for low dose CT scanning of a subject, the system comprising: (a) a pulse generator configured to be coupled to an X-ray source of a CT scanner, the X-ray source being mounted on gantry so as to rotate within a cylindrical enclosure of the CT scanner; the pulse generator configured to periodically switch off emission of X-rays from the X-ray source into the cylindrical enclosure; and (b) application software coupled to the pulse generator; the application software comprising instructions to control timing of the pulse generator so as to intermittently expose a subject to X-rays from the X-ray source at pre-specified rotation angles of the gantry.

2. The system of any preceding embodiment: wherein the pulse generator comprises a mechanical shutter coupled to the x-ray source; wherein the shutter comprises an off-state to restrict X-rays from being emitted from the X-ray source and an on-state configured to allow X-rays to be emitted from the X-ray source into the enclosure; wherein the shutter is coupled to the application software to receive said instructions; and wherein the instructions comprise commands for timing the on-state of the shutter and resulting X-ray exposure at said pre-specified rotation angles of the gantry.

3. The system of any preceding embodiment: wherein the pulse generator comprises an off-state to restrict X-rays from being emitted from the X-ray pulse generator source and an on-state configured to allow X-rays to be emitted from the X-ray source into the enclosure; and wherein the pulse generator is coupled to the X-ray source to electromagnetic shield the X-ray source from emitting X-rays in the off-state; wherein the instructions comprise commands for timing the on-state of the pulse generator and resulting X-ray exposure at said pre-specified rotation angles of the gantry.

4. The system of any preceding embodiment: wherein the X-ray source comprises an anode, a cathode and a griddling electrode there between; and wherein the pulse generator is configured to modify a negative potential of the griddling electrode to form an electromagnetic field-based shield so as to prevent electron flow from the cathode the anode, thereby stopping emission of X-rays in the off-state.

5. The system of any preceding embodiment, wherein said pre-specified angles of rotation comprise a sequence of rotation angles selected from the group of rotation schemes consisting of: an angle-bisect scheme; a Golden-ratio scheme; or a Tiny Golden-ratio scheme.

6. The system of any preceding embodiment, further comprising: application software coupled to an output of the CT scanner for receiving pulsed images from the CT scanner, the pulsed images corresponding to exposures at said pre-specified rotation angles; the application software further configured for reconstructing each of said exposures to generate a reconstructed image.

7. The system of any preceding embodiment, wherein the reconstructed image is generated via a projection view sharing techniques.

8. The system of any preceding embodiment, wherein K-space Weighted Image Contrast (KWIC) is used to generate the reconstructed image.

9. An apparatus for lowering X-ray dose to a subject in a CT scanner, the CT scanner comprising an X-ray source being mounted on gantry so as to rotate within a cylindrical enclosure of the CT scanner, and a pulse generator coupled to the X-ray source to periodically switch off emission of X-rays from the X-ray source into the cylindrical enclosure, the apparatus comprising: (a) a computer processor coupled to the CT scanner; and (b) a non-transitory computer-readable memory storing instructions executable by the computer processor; (c) wherein said instructions, when executed by the computer processor, perform steps comprising: (i) controlling timing of the pulse generator so as to intermittently expose a subject to X-rays from the X-ray source at pre-specified rotation angles of the gantry; (ii) receiving pulsed images from the CT scanner, the pulsed images corresponding to exposures at said pre-specified rotation angles; and (iii) reconstructing each of said exposures to generate a reconstructed image.

10. The apparatus of any preceding embodiment: wherein the pulse generator comprises a mechanical shutter coupled to the x-ray source; wherein the shutter comprises an off-state to restrict X-rays from being emitted from the X-ray source and an on-state configured to allow X-rays to be emitted from the X-ray source into the enclosure; wherein the shutter is coupled to the application software to receive said instructions; and wherein the instructions comprise commands for timing the on-state of the shutter and resulting X-ray exposure at said pre-specified rotation angles of the gantry.

11. The apparatus of any preceding embodiment: wherein the pulse generator comprises an off-state to restrict X-rays from being emitted from the X-ray pulse generator source and an on-state configured to allow X-rays to be emitted from the X-ray source into the enclosure; wherein the pulse generator is coupled to the X-ray source to electromagnetic shield the X-ray source from emitting X-rays in the off-state; and wherein the instructions comprise commands for timing the on-state of the pulse generator and resulting X-ray exposure at said pre-specified rotation angles of the gantry.

12. The apparatus of any preceding embodiment: wherein the X-ray source comprises an anode, a cathode and a griddling electrode there between; and wherein the instructions are configured to modify a negative potential of the griddling electrode to form an electromagnetic field-based shield so as to prevent electron flow from the cathode the anode, thereby stopping emission of X-rays in the off-state.

13. The apparatus of any preceding embodiment, wherein said pre-specified angles of rotation comprise a sequence of rotation angles selected from the group of rotation schemes consisting of: an angle-bisect scheme; a Golden-ratio scheme; or a Tiny Golden-ratio scheme.

14. The apparatus of any preceding embodiment, wherein the reconstructed image is generated via a projection view sharing techniques.

15. The apparatus of any preceding embodiment, wherein K-space Weighted Image Contrast (KWIC) is used to generate the reconstructed image.

16. A low dose CT scanner for generating CT images of a subject, the CT scanner comprising: (a) an X-ray source disposed within a cylindrical enclosure; the cylindrical enclosure comprising a plurality of detectors configured to detect X-rays emitted from the X-ray source; the X-ray source mounted on a gantry so as to rotate within the cylindrical enclosure of the CT scanner; (b) a pulse generator coupled to the X-ray source; the pulse generator configured to periodically switch off emission of X-rays from the X-ray source into the cylindrical enclosure; and (c) application software coupled to the pulse generator; the application software comprising instructions to control timing of the pulse generator so as to intermittently expose a subject to X-rays from the X-ray source at pre-specified rotation angles of the gantry.

17. The CT scanner of any preceding embodiment: wherein the pulse generator comprises a mechanical shutter coupled to the x-ray source; wherein the shutter comprises an off-state to restrict X-rays from being emitted from the X-ray source and an on-state configured to allow X-rays to be emitted from the X-ray source into the enclosure; wherein the shutter is coupled to the application software to receive said instructions; and wherein the instructions comprise commands for timing the on-state of the shutter and resulting X-ray exposure at said pre-specified rotation angles of the gantry.

18. The CT scanner of any preceding embodiment: wherein the pulse generator comprises an off-state to restrict X-rays from being emitted from the X-ray pulse generator source and an on-state configured to allow X-rays to be emitted from the X-ray source into the enclosure; wherein the pulse generator is coupled to the X-ray source to electromagnetic shield the X-ray source from emitting X-rays in the off-state; and wherein the instructions comprise commands for timing the on-state of the pulse generator and resulting X-ray exposure at said pre-specified rotation angles of the gantry 19. The CT scanner of any preceding embodiment: wherein the X-ray source comprises an anode, a cathode and a griddling electrode there between; and wherein the pulse generator is configured to modify a negative potential of the griddling electrode to form an electromagnetic field-based shield so as to prevent electron flow from the cathode the anode, thereby stopping emission of X-rays in the off-state.

20. The CT scanner of any preceding embodiment, wherein said pre-specified angles of rotation comprise a sequence of rotation angles selected from the group of rotation schemes consisting of: an angle-bisect scheme; a Golden-ratio scheme; or a Tiny Golden-ratio scheme.

21. The CT scanner of any preceding embodiment, further comprising: application software coupled to the plurality of detectors for receiving pulsed images corresponding to exposures at said pre-specified rotation angles; the application software further configured for reconstructing each of said exposures to generate a reconstructed image.

22. The CT scanner of claim 21, wherein the reconstructed image is generated via a projection view sharing techniques.

23. The CT scanner of claim 22, wherein K-space Weighted Image Contrast (KWIC) is used to generate the reconstructed image.

24. A method for lowering X-ray dose to a subject in a CT scanner, the CT scanner comprising an X-ray source mounted on gantry so as to rotate within a cylindrical enclosure of the CT scanner and emit of X-rays into the cylindrical enclosure, the method comprising: (a) intermittently exposing a subject within the enclosure to X-rays from the X-ray source at pre-specified rotation angles of the gantry; (b) receiving pulsed images from the CT scanner, the pulsed images corresponding to exposures at said pre-specified rotation angles; and (c) reconstructing each of said exposures to generate a reconstructed image.

25. The method of any preceding embodiment: wherein the CT scanner comprises a mechanical shutter coupled to the x-ray source; wherein the shutter comprises an off-state to restrict X-rays from being emitted from the X-ray source and an on-state configured to allow X-rays to be emitted from the X-ray source into the enclosure; and wherein intermittently exposing a subject comprises timing the on-state of the shutter and resulting X-ray exposure at said pre-specified rotation angles of the gantry.

26. The method of any preceding embodiment: wherein the X-ray source comprises an electron beam being focused on an anode from a cathode to generate said X-rays; and wherein intermittently exposing a subject comprises deflecting the electron beam off the anode using a magnetic field, thereby restricting emission of X-rays from the X-ray source into the enclosure to control X-ray exposure to the subject only at said pre-specified rotation angles of the gantry.

27. The method of any preceding embodiment: wherein the X-ray source further comprises a griddling electrode between the anode and the cathode; and wherein deflecting the electron beam off the anode comprises generating sufficient negative potential within the griddling electrode to form an electromagnetic field-based shield so as to prevent electron flow from the cathode the anode, thereby stopping emission of X-rays for pre-specified rotation angles.

28. The method of any preceding embodiment, wherein said pre-specified angles of rotation comprise a sequence of rotation angles selected from the group of rotation schemes consisting of: an angle-bisect scheme; a Golden-ratio scheme; or a Tiny Golden-ratio scheme.

29. The method of any preceding embodiment, wherein the reconstructed image is generated via a projection view sharing techniques.

30. The method of any preceding embodiment, wherein K-space Weighted Image Contrast (KWIC) is used to generate the reconstructed image.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for reduced dose CT scanning of a subject, the system comprising:
   (a) a pulse generator configured to be coupled to an X-ray source of a CT scanner, the X-ray source being mounted on gantry so as to rotate within a cylindrical enclosure of the CT scanner;
   (b) said pulse generator configured to periodically switch off emission of X-rays from the X-ray source, using high speed electromagnetic switching on the order of milliseconds, into the cylindrical enclosure; and
   (c) a processor configured for controlling said pulse generator and receiving an output from said CT scanner;
   (d) a non-transitory memory storing instructions executable by the processor;
   (e) wherein said instructions, when executed by the processor, perform steps comprising:
      (i) controlling timing of the pulse generator so as to intermittently expose a subject to X-rays from the X-ray source at the pre-specified rotation angles of the gantry;
      (ii) receiving pulsed images from the CT scanner, the pulsed images corresponding to exposures at said pre-specified rotation angles of said X-ray source within the cylindrical enclosure of the CT scanner;
      (iii) reconstructing each of said exposures to generate a reconstructed image based on using a K-space Weighted Image Contrast (KWIC) through projection view sharing, wherein a central 2D Fourier Transform (2DFT) space, which determines the image contrast, is sampled by projection views of a time frame of interest, and wherein a peripheral 2DFT space is filled by projection views of time frames neighboring a time frame of interest.

2. The system of claim 1:
wherein the pulse generator comprises an off-state to restrict X-rays from being emitted from the X-ray pulse generator source and an on-state configured to allow X-rays to be emitted from the X-ray source into the cylindrical enclosure;
wherein the pulse generator is coupled to the X-ray source to electromagnetically shield the X-ray source from emitting X-rays in the off-state; and
wherein said instructions when executed by the processor further perform steps comprising timing the on-state of the pulse generator and resulting X-ray exposure at said pre-specified rotation angles of the gantry.

3. The system of claim 2:
wherein the X-ray source comprises an anode, a cathode and a griddling electrode therebetween; and
wherein the pulse generator is configured to modify a negative potential of the griddling electrode to form an electromagnetic field-based shield so as to prevent electron flow from the cathode the anode, thereby stopping emission of X-rays in the off-state.

4. The system of claim 1, wherein said pre-specified rotation angles comprise a sequence of rotation angles selected from the group of rotation angle schemes consisting of: an angle-bisect scheme, a Golden-ratio scheme, and a Tiny Golden-ratio scheme.

5. An apparatus for reducing X-ray dose to a subject in a CT scanner, the CT scanner comprising an X-ray source being mounted on gantry so as to rotate within a cylindrical enclosure of the CT scanner, and a pulse generator coupled to the X-ray source to periodically switch off emission of X-rays from the X-ray source into the cylindrical enclosure, the apparatus comprising:
   (a) a computer processor coupled to the CT scanner and the pulse generator; and
   (b) a non-transitory computer-readable memory storing instructions executable by the computer processor;
   (c) wherein said instructions, when executed by the computer processor, perform steps comprising:
      (i) controlling timing of the pulse generator so as to intermittently expose a subject to X-rays from the X-ray source at pre-specified rotation angles of the gantry using high speed electromagnetic switching on the order of milliseconds;
      (ii) receiving pulsed images from the CT scanner, the pulsed images corresponding to exposures at said pre-specified rotation angles; and
      (iii) reconstructing each of said exposures to generate a reconstructed image based on using a K-space Weighted Image Contrast (KWIC) through projection view sharing, wherein a central 2D Fourier Transform (2DFT) space, which determines the image contrast, is sampled by projection views of a time frame of interest, and wherein a peripheral 2DFT space is filled by projection views of time frames neighboring a time frame of interest.

6. The apparatus of claim 5:
wherein the pulse generator comprises an off-state to restrict X-rays from being emitted from the X-ray pulse generator source and an on-state configured to allow X-rays to be emitted from the X-ray source into the cylindrical enclosure;
wherein the pulse generator is coupled to the X-ray source to electromagnetically shield the X-ray source from emitting X-rays in the off-state; and
wherein said instructions when executed by the processor perform steps comprising timing the on-state of the pulse generator and resulting X-ray exposure at said pre-specified rotation angles of the gantry.

7. The apparatus of claim 6:
wherein the X-ray source comprises an anode, a cathode and a griddling electrode there between therebetween; and
wherein said instructions when executed by the processor perform steps comprising controlling said X-ray source to modify a negative potential of the griddling electrode to form an electromagnetic field-based shield so as to prevent electron flow from the cathode the anode, thereby stopping emission of X-rays in the off-state.

8. The apparatus of claim 5, wherein said pre-specified angles of rotation comprise a sequence of rotation angles selected from a group of rotation angle schemes consisting of: an angle-bisect scheme, a Golden-ratio scheme, and a Tiny Golden-ratio scheme.

9. A reduced dose CT scanner for generating CT images of a subject, the CT scanner comprising:
   (a) an X-ray source disposed within a cylindrical enclosure, wherein the cylindrical enclosure comprising a plurality of detectors configured to detect X-rays emitted from the X-ray source, and in which the X-ray source is mounted on a gantry configured to rotate within the cylindrical enclosure of the CT scanner;

(b) a pulse generator coupled to the X-ray source, wherein the pulse generator is configured to periodically switch off emission of X-rays from the X-ray source using high speed electromagnetic switching on the order of milliseconds into the cylindrical enclosure; and (c) a computer processor or server coupled to the pulse generator and the plurality of detectors for receiving pulsed images corresponding to exposures at pre-specified rotation angles of the X-ray source within the cylindrical enclosure;

(d) a non-transitory memory storing instructions executable by the processor;

(e) wherein said instructions, when executed by the computer processor or server, perform steps comprising:
  (i) timing of the pulse generator which is configured to intermittently expose a subject to X-rays from the X-ray source at pre-specified rotation angles of the gantry;
  (ii) receiving pulsed images from the CT scanner, the pulsed images corresponding to exposures at said pre-specified rotation angles;
  (iii) reconstructing each of said exposures to generate a reconstructed image based on using a K-space Weighted Image Contrast (KWIC) through projection view sharing, wherein a central 2D Fourier Transform (2DFT) space, which determines the image contrast, is sampled by projection views of a time frame of interest, and wherein a peripheral 2DFT space is filled by projection views of time frames neighboring a time frame of interest.

10. The CT scanner of claim 9:
wherein the pulse generator is configured with an off-state to restrict X-rays from being emitted from the X-ray pulse generator source and an on-state configured to allow X-rays to be emitted from the X-ray source into the cylindrical enclosure;
wherein the pulse generator is coupled to the X-ray source to electromagnetically shield the X-ray source from emitting X-rays in the off-state; and
wherein said instructions when executed by the computer processor or server perform steps comprising timing the on-state of the pulse generator and resulting X-ray exposure at said pre-specified rotation angles of the gantry.

11. The CT scanner of claim 10:
wherein the X-ray source comprises an anode, a cathode and a griddling electrode therebetween; and
wherein the pulse generator is configured to modify a negative potential of the griddling electrode to form an electromagnetic field-based shield so as to prevent electron flow from the cathode the anode, thereby stopping emission of X-rays in the off-state.

12. The CT scanner of claim 9, wherein said pre-specified angles of rotation comprise a sequence of rotation angles selected from group of rotation angle schemes consisting of: an angle-bisect scheme, a Golden-ratio scheme, and a Tiny Golden-ratio scheme.

13. A method for reducing X-ray dose upon a subject in a CT scanner, the CT scanner comprising an X-ray source mounted on gantry so as to rotate within a cylindrical enclosure of the CT scanner and emit of X-rays into the cylindrical enclosure, the method comprising:
  (a) intermittently exposing a subject within the enclosure to X-rays from the X-ray source using high speed electromagnetic switching on the order of milliseconds at pre-specified rotation angles of the gantry;
  (b) receiving pulsed images from the CT scanner, the pulsed images corresponding to exposures at said pre-specified rotation angles; and
  (c) reconstructing each of said exposures to generate a reconstructed image based on using a K-space Weighted Image Contrast (KWIC) through projection view sharing, wherein a central 2D Fourier Transform (2DFT) space, which determines the image contrast, is sampled by projection views of a time frame of interest, and wherein a peripheral 2DFT space is filled by projection views of time frames neighboring a time frame of interest.

14. The method of claim 13:
wherein the X-ray source comprises focusing an electron beam on an anode from a cathode for generating said X-rays; and
wherein intermittently exposing a subject comprises deflecting the electron beam off the anode using a magnetic field, thereby restricting emission of X-rays from the X-ray source into the cylindrical enclosure to control X-ray exposure to the subject only at said pre-specified rotation angles of the gantry.

15. The method of claim 14, further comprising interposing a griddling electrode between the anode and the cathode of the X-ray source for
deflecting the electron beam off the anode in response to generating sufficient negative potential within the griddling electrode to form an electromagnetic field-based shield so as to prevent electron flow from the cathode the anode, thereby stopping emission of X-rays for pre-specified rotation angles.

16. The method of claim 13, further comprising selecting of said pre-specified angles of rotation in response to utilizing a sequence of rotation angles selected from a group of rotation angle schemes consisting of: an angle-bisect scheme, a Golden-ratio scheme, and a Tiny Golden-ratio scheme.

\* \* \* \* \*